(12) United States Patent
Baba

(10) Patent No.: US 8,526,112 B2
(45) Date of Patent: Sep. 3, 2013

(54) CAPSULE ENDOSCOPE

(75) Inventor: Tomoyuki Baba, Saitama (JP)

(73) Assignee: FUJIFILM Corporation, Tokyo (JP)

( * ) Notice: Subject to any disclaimer, the term of this patent is extended or adjusted under 35 U.S.C. 154(b) by 41 days.

(21) Appl. No.: 13/259,192

(22) PCT Filed: Mar. 24, 2010

(86) PCT No.: PCT/JP2010/055141
§ 371 (c)(1),
(2), (4) Date: Sep. 23, 2011

(87) PCT Pub. No.: WO2010/110350
PCT Pub. Date: Sep. 30, 2010

(65) Prior Publication Data
US 2012/0022327 A1   Jan. 26, 2012

(30) Foreign Application Priority Data

Mar. 24, 2009   (JP) .................................. 2009-071919

(51) Int. Cl.
*G02B 21/28* (2006.01)
(52) U.S. Cl.
USPC .......................... 359/642; 600/101; 600/109
(58) Field of Classification Search
USPC ............... 359/656–661, 738, 725, 642, 648, 359/800; 600/179, 101; 250/208.1
See application file for complete search history.

(56) References Cited

U.S. PATENT DOCUMENTS

| 7,317,180 | B2 * | 1/2008 | Konno et al. | ............. 250/208.1 |
| 7,319,896 | B2 | 1/2008 | Konno | |
| 8,254,038 | B2 * | 8/2012 | Togino | ......................... 359/725 |
| 2005/0054901 | A1 | 3/2005 | Yoshino | |
| 2005/0054902 | A1 | 3/2005 | Konno | |
| 2005/0124858 | A1 | 6/2005 | Matsuzawa et al. | |
| 2006/0244822 | A1 | 11/2006 | Konno et al. | |
| 2009/0015935 | A1 * | 1/2009 | Szapiel et al. | ................ 359/674 |
| 2009/0306477 | A1 * | 12/2009 | Togino | ........................ 600/176 |
| 2009/0310230 | A1 | 12/2009 | Togino | |

FOREIGN PATENT DOCUMENTS

| CN | 201039978 Y | 3/2008 |
| CN | 101380219 A | 3/2009 |
| EP | 2 033 570 A1 | 3/2009 |
| JP | 2002-116491 A | 4/2002 |

(Continued)

OTHER PUBLICATIONS

First Office Action, dated Nov. 5, 2012, issued in corresponding CN Application No. 201080013174.1, 14 pages in English and Chinese.

(Continued)

*Primary Examiner* — Jordan Schwartz
*Assistant Examiner* — William Alexander
(74) *Attorney, Agent, or Firm* — Sughrue Mion, PLLC

(57) ABSTRACT

A capsule endoscope is provided with an imaging lens, capsule body, and a transparent cover. The capsule body is formed hollow, and has an opening at an end. The imaging lens is provided such that a part thereof is positioned inside the capsule body and the rest is protruded from the opening. The transparent cover is formed into a dope shape, and is attached to the end of the capsule body to cover the imaging lens protruded from the opening. The inside of a patient's body is captured using the transparent cover and the imaging lens designed to satisfy the following condition: $|f_D|/f_L \leq 70$ where $f_D$ is a focal length of the transparent cover, and $f_L$ is a focal length of the imaging lens.

11 Claims, 9 Drawing Sheets

(56) References Cited

FOREIGN PATENT DOCUMENTS

| | | |
|---|---|---|
| JP | 2005-080789 A | 3/2005 |
| JP | 2005-080790 A | 3/2005 |
| JP | 2006-061438 A | 3/2006 |
| JP | 2006-304924 A | 11/2006 |
| JP | 2008-040468 A | 2/2008 |
| JP | 2008-197541 A | 8/2008 |
| JP | 2008-309860 A | 12/2008 |
| WO | WO 2008-004377 * | 1/2008 |

OTHER PUBLICATIONS

International Search Report, mailed Jun. 15, 2010, issued in corresponding International Application No. PCT/JP2010/055141, 7 pages in English and Japanese.

Notification of Reasons for Refusal, dated Feb. 27, 2013, issued in corresponding JP Application No. 2009-071919, 8 pages in English and Japanese.

* cited by examiner $(Y(\omega+\Delta\omega)-Y(\omega))/Y(\Delta\omega)$

CAPSULE ENDOSCOPE

TECHNICAL FIELD

The present invention relates to a capsule endoscope that is swallowed by a patient and used for imaging the inside of a body cavity.

BACKGROUND ART

In the medical field, a capsule endoscope in which an image sensor is stored in a capsule is now used for a diagnosis, in addition to an insertion-type endoscope having the image sensor provided at a distal end of a long insert section.

The capsule endoscope has a hollow capsule body, a dome-shaped transparent cover attached to one end of the capsule body, and an imaging lens that forms an image from light entered through the transparent cover on an image sensor. The capsule endoscope is formed in such a size that the patient can easily swallow (see Patent Documents 1 to 3). Owing to this, the capsule endoscope eliminates burden on a patient occurred in the diagnosis using the insertion-type endoscope, such as swallowing the insert section of the endoscope into his/her mouth or being kept inserting the insert section through the body for long periods of time.

PRIOR ART DOCUMENTS

Patent Documents
Patent Document 1: JP 2006-61438 A
Patent Document 2: JP 4128504 B
Patent Document 3: JP 4128505 B

SUMMARY OF INVENTION

Problems to be Solved by the Invention

While the capsule endoscope has an advantage in that it solves the problems of the insertion-type endoscope, it is difficult to control the position and orientation of the capsule endoscope inside the body cavity, unlike the insertion-type endoscope. Therefore, even though a lesion can be surely captured when the lesion is situated at the center of a subject, the lesion cannot be surely captured when the lesion is situated, for example, at the periphery of the transparent cover or near sides of the capsule body.

In view of this, it is necessary to use a wide-angle imaging lens to surely capture the lesion. However, it is difficult to produce the imaging lens that is capable of capturing even the lesion at the periphery of the transparent cover, which may have a maximum angle of view of, for example, more than 180°. In addition, since the imaging lens has a tendency that its aberration increases as the angle of view increases, the obtained image may be distorted or blurred even if the lesion is captured. It is difficult to find the lesion in the image being distorted like this.

Means for Solving the Problems

The present invention is made in view of the above-described background, and has an object to provide a capsule endoscope that has a wider angle of view and capable of obtaining a clear image with no distortion by sufficiently correcting an aberration caused by widening the angle of view.

In order to achieve the above object, a capsule endoscope of the present invention includes a hollow capsule body having an opening at its end, an imaging optical system provided inside the capsule body or provided to protrude from the opening of the capsule body, and a transparent cover attached to the end of the capsule body to cover the imaging optical system. In the capsule endoscope of the present invention, the inside of a body cavity of a patient is captured with the transparent cover and the imaging optical system satisfying the following condition:

$$|f_D|/f_L \leq 70$$

where $f_D$ is a focal length of the transparent cover, and $f_L$ is a focal length of the imaging optical system.

In the capsule endoscope including a hollow capsule body having an opening at its end, an imaging optical system provided inside the capsule body or provided to protrude from the opening of the capsule body, and a transparent cover attached to the end of the capsule body to cover the imaging optical system, the inside of a body cavity of a patient is captured with the transparent cover and the imaging optical system satisfying the following condition:

$$2\omega_{max} - 2\omega_L \geq 2.5$$

where $2\omega_{max}$ is a maximum angle of view of the imaging optical system and the transparent cover as a whole, and $2\omega_L$ is a maximum angle of view of the imaging optical system only.

Moreover, the present invention makes it possible to surely capture a lesion that is situated at the periphery of the transparent cover by satisfying the following condition:

$$2\omega_{max} \geq 180°$$

where $2\omega_{max}$ is a maximum angle of view of the imaging optical system and the transparent cover as a whole.

The present invention makes it possible to reduce distortion of the lesion that appears at the periphery of the captured image, and thereby preventing an oversight of the lesion by satisfying the following condition:

$$0.7 < (Y(\omega + \Delta\omega) - Y(\omega))/Y(\Delta\omega)$$

where $Y(\omega)$ is an image height at an arbitrary angle of view $\omega$, and $\Delta\omega$ is an amount of slight change in the arbitrary angle of view $\omega$.

The present invention can provide superior imaging performance when the imaging optical system is constituted of four lenses, and more preferably constituted of five lenses.

Effect of the Invention

According to the present invention, the angle of view can be widened and also a clear image with no distortion can be obtained by sufficiently correcting an aberration caused by widening the angle of view.

MODE FOR CARRYING OUT THE INVENTION

Figure 1:
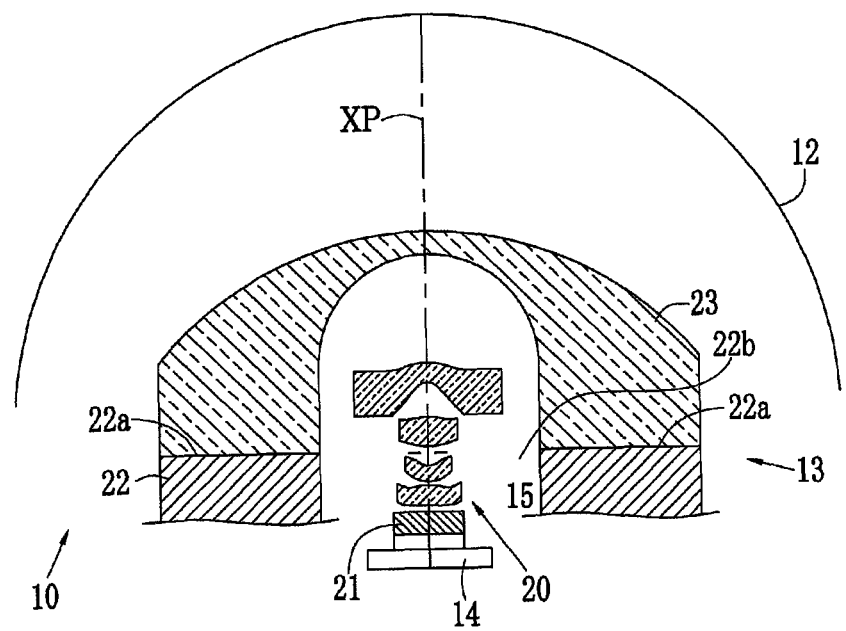
FIG. 1 is a cross-sectional view illustrating a capsule endoscope of the present invention.

As shown in FIG. 1, a capsule endoscope 10 is formed in such a size that it can be swallowed by a patient with ease, and captures images inside the stomach or intestines during the period from being swallowed until excretion from the body at constant time intervals. In this embodiment, a subject 12 of concave sphere is explained as a subject to be captured with the capsule endoscope 10. Note that the shape of the subject is not limited to the concave sphere but may be in other concave curved forms.

Figure 2:
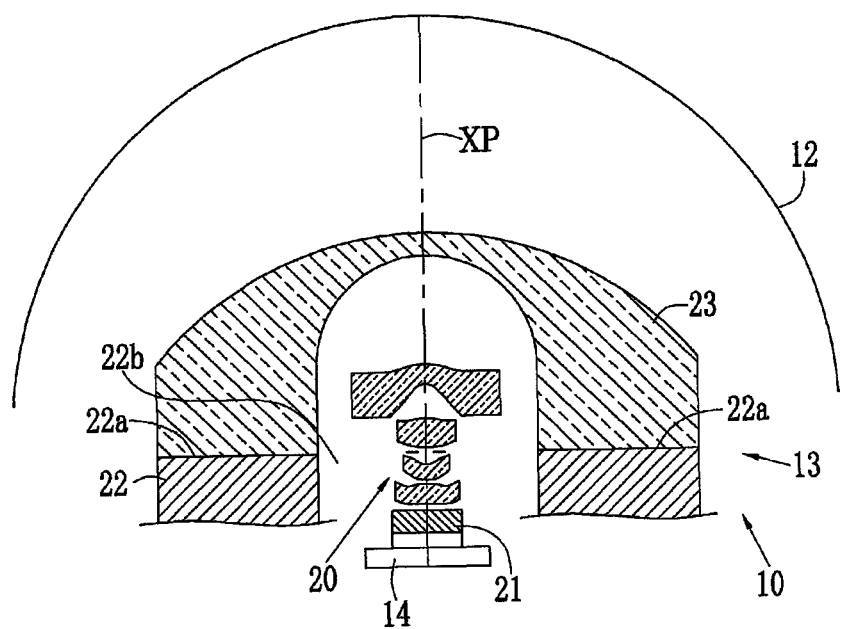
FIG. 2 is a cross-sectional view illustrating the capsule endoscope of the present invention viewed from a direction which is rotated 90 degrees clockwise from FIG. 1.

As shown in FIG. 1 and FIG. 2 illustrating the capsule endoscope 10 viewed from a direction which is rotated 90 degrees clockwise from FIG. 1, the capsule endoscope 10 is provided with a capsule 13, an image sensor 14, an imaging lens 20, and a cover glass 21. The capsule 13 has a capsule body 22 and a transparent cover 23. The capsule body 22 is formed hollow, and has an opening 22b at its end 22a. The imaging lens 20 is provided such that a part thereof is positioned inside the capsule body 22 and the rest is protruded from the opening 22b. The transparent cover 23 is formed into a dome shape, and is attached to the end 22a of the capsule body 22 to cover the imaging lens 20 protruded from the opening 22b. Depending on the design conditions of the lens, the whole imaging lens may be protruded from the opening of the capsule body, or the whole imaging lens may be provided inside the capsule body.

The imaging lens 20 and transparent cover 23 have optical power for forming an image from light from the subject 12 on the image sensor 14. On the other hand, the cover glass 21 transmits the light from the subject 12 without refracting it, which means has no optical power like the imaging lens 20 and transparent cover 23. The material of the transparent cover 23 may be the same as the imaging lens 20 and not particularly limited.

In addition to the image sensor 14, a battery (not shown) for driving the image sensor 14, an antenna (not shown) for sending the image captured with the image sensor 14 to image receivers (not shown) attached to the patient, and the like are stored inside the capsule body 22.

Figure 3:
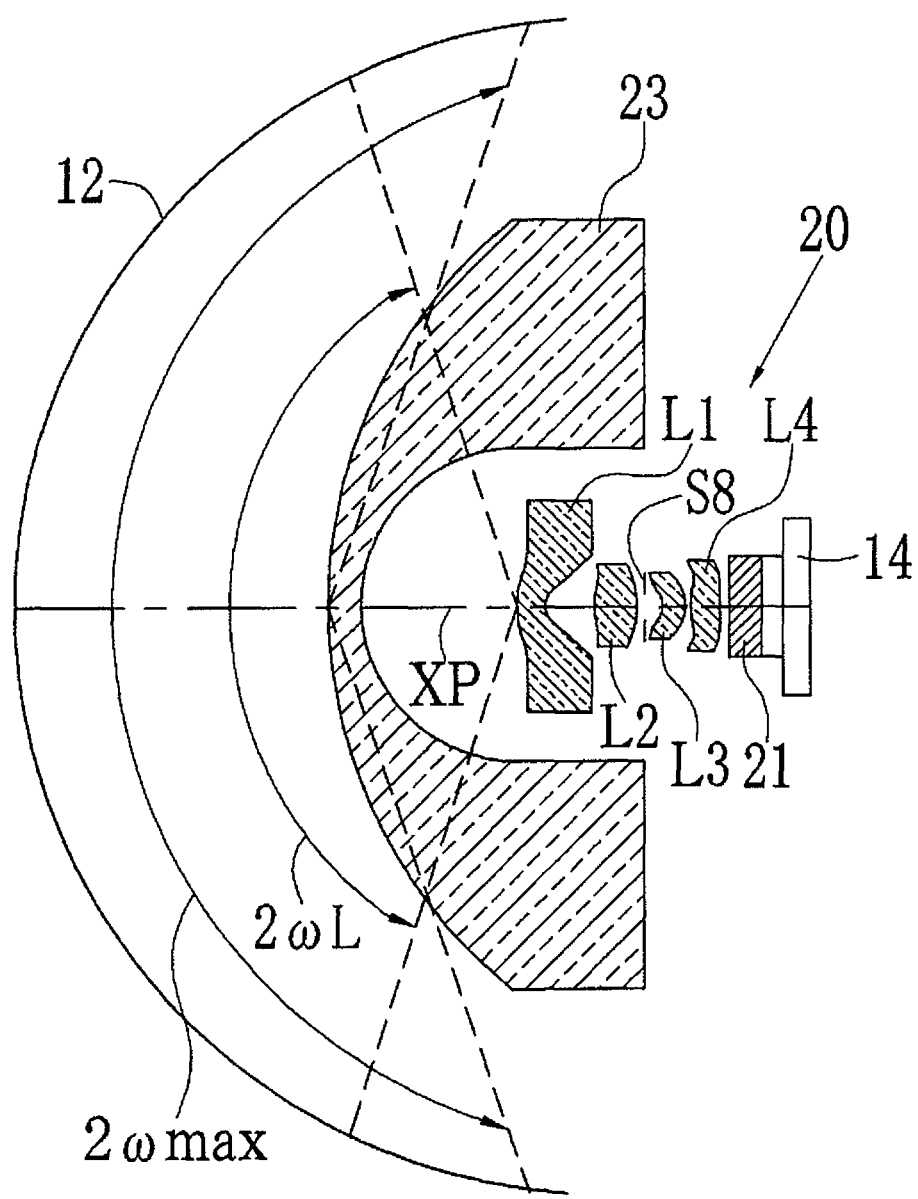
FIG. 3 is a cross-sectional view of the capsule endoscope of the present invention used for explaining mathematical expression 1 to mathematical expression 3.

As shown in FIG. 3, the imaging lens 20 is constituted of a first lens L1, a second lens L2, an aperture stop S8, a third lens L3, and a fourth lens L4, arranged in this order from the subject 12 side. The transparent cover 23 is provided between the subject 12 and the first lens L1.

Here, the imaging lens 20 and transparent cover 23 are designed to satisfy the following mathematical expression 1:

$$|f_D|/f_L \leq 70 \quad \text{[Mathematical Expression 1]}$$

where a focal length of the transparent cover 23 is defined as $f_D$ and a focal length of the whole imaging lens 20 is defined as $f_L$.

When the imaging lens 20 and transparent cover 23 satisfy the mathematical expression 1 while providing the transparent cover 23 with the optical power of forming an image from the light from the subject 12 on the image sensor 14, an angle of view is widened more. Owing to this, even a lesion which is situated at the periphery of the transparent cover 23 can also be surely captured. Even though the angle of view is widened, an aberration caused by widening the angle of view is sufficiently corrected, and therefore a clear image with no distortion or blurring can be obtained. When $|f_D|/f_L$ is more than 70, the refractive power of the transparent cover 23 becomes small. As a result, the wide angle of view has to be achieved only with the imaging lens 20, which makes it difficult to correct aberrations.

In addition, the imaging lens 20 and transparent cover 23 are designed to satisfy the following mathematical expression 2:

$$2\omega_{max} - 2\omega_L \geq 2.5 \quad \text{[Mathematical Expression 2]}$$

where $2\omega_{max}$ is a maximum angle of view of the imaging lens 20 and transparent cover 23 as a whole, and $2\omega_L$ is a maximum angle of view of the imaging lens 20 only.

When the imaging lens 20 and transparent cover 23 satisfy the mathematical expression 2 while providing the transparent cover 23 with the optical power of forming an image from the light from the subject 12 on the image sensor 14, the lesion situated within the angle of view of the imaging lens 20 and transparent cover 23 as a whole can be surely captured, even if the lesion is not situated within the angle of view of the imaging lens 20. Even though the angle of view is widened, an aberration caused by widening the angle of view is sufficiently corrected, and therefore a clear image with no distortion or blurring can be obtained on the image sensor 14. When $2\omega_{max} - 2\omega_L$ is less than 2.5, the refractive power of the transparent cover 23 becomes small. As a result, the wide angle of view has to be achieved only with the imaging lens 20, which makes it difficult to correct aberrations.

Moreover, the imaging lens 20 and transparent cover 23 are designed to satisfy the following mathematical expression 3:

$$2\omega_{max} \geq 180° \quad \text{[Mathematical Expression 3]}$$

When the imaging lens 20 and transparent cover 23 satisfy the mathematical expression 3, an angle of view is widened more. Owing to this, even a lesion which is situated at the periphery of the transparent cover 23 can also be surely captured. Even though the angle of view is widened, an aberration caused by widening the angle of view is sufficiently corrected, and therefore a clear image with no distortion or blurring can be obtained even when the lesion situated at the periphery of the transparent cover 23 is captured.

Further, the imaging lens 20 and transparent cover 23 are designed to satisfy the following mathematical expression 4:

$$0.7 < \frac{Y(\omega + \Delta\omega) - Y(\omega)}{Y(\Delta\omega)} \quad \text{[Mathematical Expression 4]}$$

where $Y(\omega)$ is an image height at an angle of view $\omega$. Note that the mathematical expression 4 may be satisfied under the condition that the angle of view is 105° or less.

In the mathematical expression 4, "$Y(\omega+\Delta\omega)-Y(\omega)$" indicates a difference between an image height $Y(\omega+\Delta\omega)$ at an angle of view $\omega+\Delta\omega$, in which a slight change, such as from $\omega$ to $\Delta\omega$, is made in the angle of view, and the image height $Y(\omega)$ at the angle of view $\omega$. Moreover, "$Y(\Delta\omega)$" in the mathematical expression 4 indicates a difference $Y(0+\Delta\omega)-$ Y(0) between the image height Y(Δω) at the angle of view Δω, in which a slight change, such as from 0° to Δω, is made in the angle of view, and the image height Y(0) at the angle of view 0°. Since Y(0) is equal to 0, Y(0+Δω)−Y(0) is equal to Y(Δω). Accordingly, the part "(Y(ω+Δω)−Y(ω))/Y(Δω)" in the mathematical expression 4 represents a degree of distortion at periphery area of the image with respect to a center area of the image.

Figure 4C:
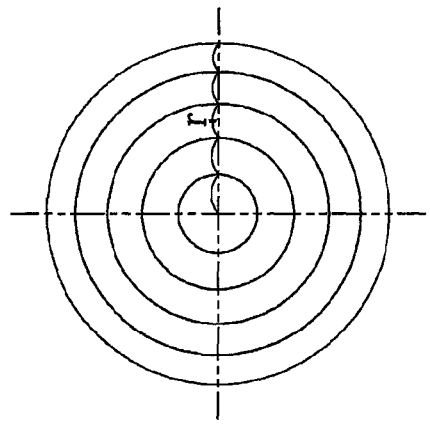
FIGS. 4B to 4E are diagrams each illustrating an image capturing the plurality of circles of FIG. 4A.
Figure 4E:
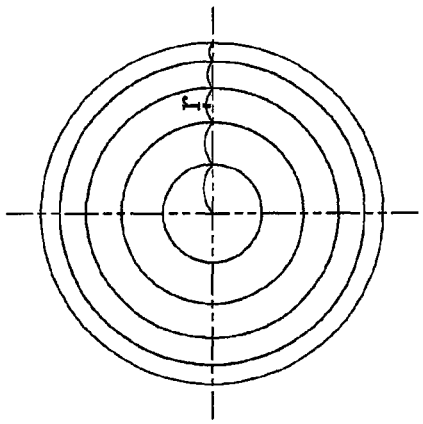

Here, four combinations of the imaging lens 20 and transparent cover 23 are designed such that (Y(ω+Δω)−Y(ω))/Y(Δω) respectively is 1.0, 0.7, 0.5 and 0.3. The image captured with each combination of the imaging lens and transparent cover is evaluated in view of degree of distortion. In the evaluation, as shown in FIG. 4A, circles 30a to 30e with a radius of r, 2r, 3r, 4r, and 5r, respectively are provided concentrically on the subject 12 of concave sphere at regular intervals of distance r. Then, the subject 12 with the circles 30a to 30e is captured using each pair of the imaging lens and transparent cover. On the captured image, distance between the adjacent circles is compared between the periphery area and the center area of the image. The degree of distortion at the periphery area of the image is evaluated by checking how much the distance between the circles contracted at the periphery area as compared to that at the center area.

Figure 4B:
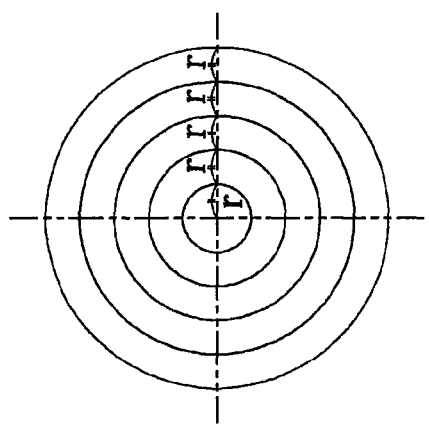

FIG. 4B shows the image captured with a combination of the imaging lens 20 and transparent cover 23 which satisfies the following condition: (Y(ω+Δω))−Y(ω))/Y(Δω)=1.0. As can be seen from the image, the distance interval between the adjacent circles on the image is equal to the distance r which is the distance between the adjacent circles of the circles 30a to 30e provided on the subject 12. Since the distance between the adjacent circles at the center area of the image is same as the distance between the adjacent circles at the periphery area of the image, the distortion does not occur at the periphery area of the image. Accordingly, when an image inside the body of the patient is captured with the capsule endoscope 10 provided with the imaging lens 20 and transparent cover 23 configured as such, the lesion appearing at the periphery area in the image is not distorted, and therefore the lesion can be surely found.

FIG. 4C shows the image captured with a combination of the imaging lens 20 and transparent cover 23 which satisfies the following condition: (Y(ω+Δω)−Y(ω)))/Y(Δω))=0.7. As can be seen from the image, the distance between the adjacent circles at the center area of the image is larger than the distance r, while the distance between the adjacent circles at the periphery area of the image is smaller than the distance r. That is, the distance between the adjacent circles is smaller at the periphery area of the image as compared to the center area of the image, however, the contraction in the distance between the adjacent circles at the periphery area is not so distinguishable. Accordingly, when an image inside the body of the patient is captured with the capsule endoscope 10 provided with the imaging lens 20 configured as such, the lesion appearing at the periphery area in the image is distorted to the extent that the distortion may be or may not be barely negligible in the diagnosis using the image.

Figure 4D:
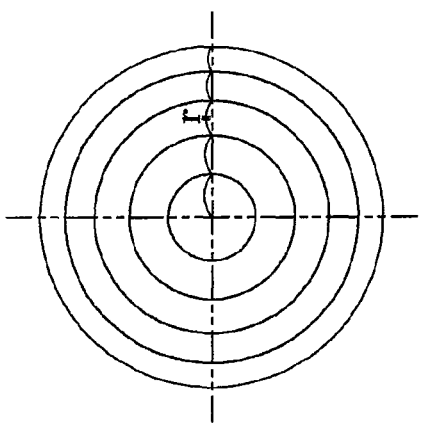
Figure 4A:
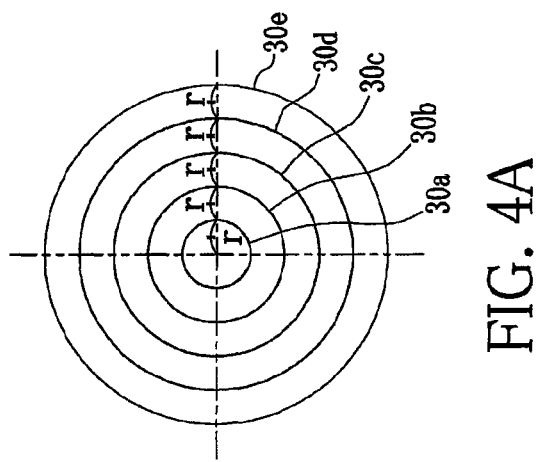
FIG. 4A is a diagram illustrating a plurality of circles provided on a subject of concave sphere.

FIG. 4D shows the image captured with a combination of the imaging lens 20 and transparent cover 23 which satisfies the following condition: (Y(ω+Δω)−Y(ω))/Y(Δω)=0.5. As can be seen from the image, the distance between the adjacent circles is smaller at the periphery area of the image as compared to the distance between the adjacent circles at the center area of the image, and the contraction in the distance between the adjacent circles at the periphery area of the image is distinguishable. Hence, it is known that the distortion occurred at the periphery area of the image. Accordingly, when an image inside the body of the patient is captured with the capsule endoscope 10 provided with the imaging lens 20 and transparent cover 23 configured as such, the periphery area in the image is distorted, and therefore the lesion may be overlooked.

FIG. 4E shows the image captured with a combination of the imaging lens 20 and transparent cover 23 which satisfies the following condition: (Y(ω+Δω)−Y(ω))/Y(Δω)=0.3. As can be seen from the image, the distance between the adjacent circles is extremely smaller at the periphery area of the image as compared to the distance between the adjacent circles at the center area of the image, and the contraction in the distance between the adjacent circles at the periphery area of the image is conspicuous at a glance of the image. Hence, it is known that the distortion occurred at the periphery area of the image. Accordingly, when an image inside the body of the patient is captured with the capsule endoscope provided with the imaging lens 20 and transparent cover 23 configured as such, the periphery area in the image is extremely distorted, and therefore the lesion will most likely be overlooked.

In view of the above results, the distortion at the periphery area of the image can be suppressed by designing the imaging lens 20 and transparent cover 23 to satisfy the following condition: (Y(ω+Δω)−Y(ω))/Y(Δω)>0.7. When the condition is satisfied, the lesion, even if it appears at the periphery area of the image, will not be distorted to the extent that it is overlooked, and therefore the lesion can be surely found. Note that the amount calculated by the following condition: (Y(ω+Δω)−Y(ω))/Y(Δω) is preferably more than 0.7 and less than 1.3, and more preferably more than 0.8 and less than 1.2.

In addition, since the imaging lens 20 is constituted of four lenses: the first to fourth lenses, the angle of view is widened more, and therefore the lesion situated at the periphery of the transparent cover 23 can be captured. Even though the angle of view is widened, an aberration caused by widening the angle of view is sufficiently corrected, and therefore a clear image with no distortion or blurring can be obtained in capturing the lesion situated at the periphery of the transparent cover 23. Note that if the imaging lens is constituted of five lenses of first to fifth lenses, the same effect can be obtained as the imaging lens constituted of four lenses.

In the above embodiment, the capsule endoscope whose position and orientation inside the body of the patient are not controlled is used for explanation, however, the present invention is not limited to this. The present invention is also applicable to capsule endoscopes whose position and orientation are controllable inside the patient's body.

EMBODIMENT

Hereinafter, the present invention is explained more in detail by showing concrete numerical values in the following Embodiments 1 and 2 as to the imaging lens and transparent cover mounted on the capsule endoscope.

[Embodiment1]

Figure 5:
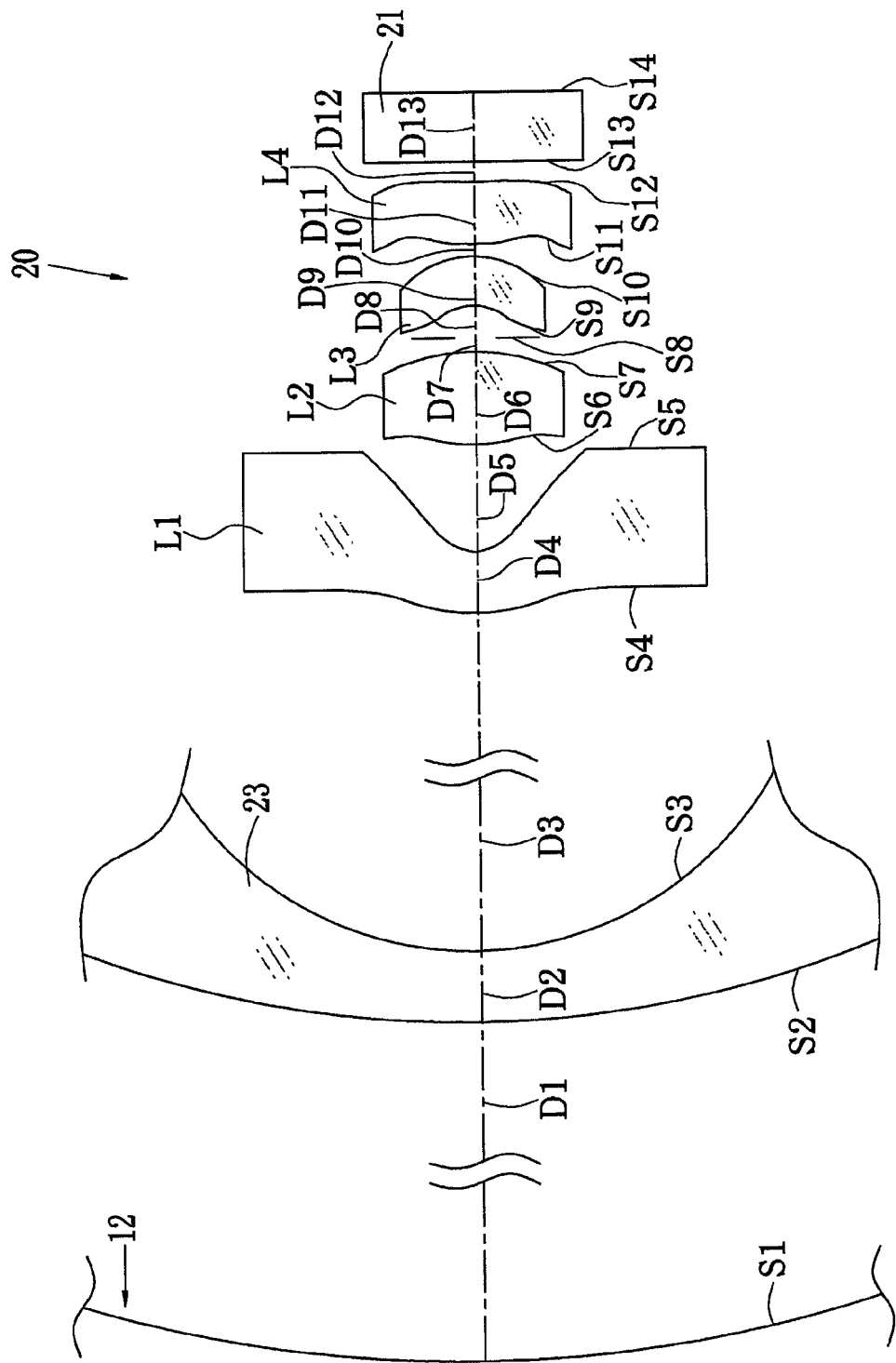
FIG. 5 is a cross-sectional view illustrating configurations of imaging lens and transparent cover according to Embodiment 1.

As shown in FIG. 5, the imaging lens 20 in Embodiment 1 includes four lenses of first lens L1 to fourth lens L4, and an aperture stop S8. Inside the capsule 13, the first lens L1, second lens L2, aperture stop S8, third lens L3, and fourth lens L4 are arranged in this order from the side of the subject 12 of concave sphere. The transparent cover 23 is disposed between the subject 12 and the first lens L1.

Surfaces of the subject 12, the transparent cover 23, and the imaging lens 20 are represented by Si. That is, the surface of the subject 12 is S1, the surface of the transparent cover 23 on the subject 12 side (hereinafter referred to as the "subject side") is S2, the surface of the transparent cover 23 on the image sensor 14 side (hereinafter referred to as the "image side") is S3, the surface of the first lens L1 on the subject side is S4, the surface of the first lens L1 on the image side is S5, the surface of the second lens L2 on the subject side is S6, the surface of the second lens L2 on the image side is S7, the aperture stop is S8, the surface of the third lens L3 on the subject side is S9, the surface of the third lens L3 on the image side is S10, the surface of the fourth lens L4 on the subject side is S11, the surface of the fourth lens L4 on the image side is S12, the surface of the cover glass 21 on the subject side is S13, and the surface of the cover glass 21 on the image side is S14. The surface S14 coincides with an imaging surface of the image sensor 14.

In addition, a distance between the surface Si and the surface S(i+1) (hereinafter referred to as surface separation) in a direction of an optical axis of the imaging lens 20 is represented by Di. That is, a surface separation between the surfaces S1 and S2 is D1, a surface separation between the surfaces S2 and S3 is D2, a surface separation between the surfaces S3 and S4 is D3, a surface separation between the surfaces S4 and S5 is D4, a surface separation between the surfaces S5 and S6 is D5, a surface separation between the surfaces S6 and S7 is D6, a surface separation between the surfaces S7 and S8 is D7, a surface separation between the surfaces S8 and S9 is D8, a surface separation between the surfaces S9 and S10 is D9, a surface separation between the surfaces S10 and S11 is D10, surface separation between the surfaces S11 and S12 is D11, a surface separation between the surfaces S12 and S13 is D12, and a surface separation between the surfaces S13 and S14 is D13.

The imaging lens 20 and transparent cover 23 are designed based on lens data shown in Table 1 below.

TABLE 1

$f_L = 1.5$
$f_D = -24.7$
Fno = 2.0
$|f_D|/f_L = 16.5$
$2\omega_{max} = 233°$
$2\omega_L = 159°$
$2\omega_{max} - 2\omega_L = 74°$

| SURFACE | CURVATURE RADIUS | SURFACE SEPARATION | Nd | vd |
|---|---|---|---|---|
| OBJ | 37.7888 | 18.8944 | | |
| 2 | 31.1292 | 1.8894 | 1.58600 | 55.0 |
| 3 | 9.6958 | 9.4470 | | |
| 4* | 2.8769 | 1.6986 | 1.53039 | 55.2 |
| 5* | 0.8065 | 3.0030 | | |
| 6* | 5.4945 | 2.5758 | 1.63178 | 23.2 |
| 7* | −5.1295 | 0.2486 | | |
| STOP | ∞ | 0.3526 | | |
| 9* | −8.3170 | 1.7502 | 1.54378 | 55.7 |
| 10* | −2.7705 | 0.3117 | | |

TABLE 1-continued $f_L = 1.5$
$f_D = -24.7$
Fno = 2.0
$|f_D|/f_L = 16.5$
$2\omega_{max} = 233°$
$2\omega_L = 159°$
$2\omega_{max} - 2\omega_L = 74°$

| SURFACE | CURVATURE RADIUS | SURFACE SEPARATION | Nd | vd |
|---|---|---|---|---|
| 11* | 5.0793 | 1.7364 | 1.54378 | 55.7 |
| 12* | −7.4451 | 0.6228 | | |
| 13 | ∞ | 1.8894 | 1.5592 | 53.9 |
| 14 | ∞ | 0.0000 | | |
| IMG | ∞ | | | |

In Table 1, "OBJ" represents the subject 12 of concave sphere, "STOP" represents the aperture stop S8, "IMG" represents the image sensor 14, "CURVATURE RADIUS" represents the curvature radius (mm) of each surface Si, "SURFACE SEPARATION" represents the distance Di between the surfaces Si and S (i+1) (mm), "Nd" represents refractive index for d-line (wavelength of 587.6 nm), "vd" represents Abbe's number, "$f_L$" represents the focal length of the imaging lens 20 as a whole, "$f_D$" represents the focal length of the transparent cover 23, "Fno" represents F number of the imaging lens 20, "$2\omega_{max}$" represents the maximum angle of view of the imaging lens 20 and transparent cover 23 as a whole, and "$2\omega_L$" represents the maximum angle of view of the imaging lens 20 only.

In Table 1, a symbol "*" in the column of the surface number indicates an aspheric surface. That is, the surfaces S4 and S5 of the first lens L1, the surfaces S6 and S7 of the second lens L2, the surfaces S9 and S10 of the third lens L3, and the surfaces S11 and S12 of the fourth lens L4 are the aspheric surfaces. These aspheric surfaces can be numerically represented by the following mathematical expression 5 with use of a curvature (reciprocal of paraxial curvature radius R) c, a conic constant K, a distance from the optical axis $\rho(\rho^2=x^2+y^2)$, and an aspherical degree of ith number. The conic constant K and an aspherical constant Ai of the surfaces S4, S5, S6, S7, S9, S10, S11, and S12 are respectively shown in Table 2. Note that the citation of the lens data and the mathematical expression 5 for determining the shape of the aspheric surface are the same in Embodiment 2 which is described later.

$$z = \frac{c\rho^2}{1 + \sqrt{1 - (K+1)c^2\rho^2}} + \sum_i A_i \rho^i \quad \text{[Mathematical Expression 5]}$$

$$(\rho^2 = x^2 + y^2)$$

TABLE 2

| SURFACE | K | A3 | A4 | A5 |
|---|---|---|---|---|
| 4 | −1.0000 | −4.2355E−02 | 9.1919E−04 | 3.3623E−04 |
| 5 | −1.0000 | −1.4101E−01 | 3.6825E−02 | −7.8345E−03 |
| 6 | −1.0000 | −1.2412E−02 | 3.2105E−02 | −3.1943E−02 |
| 7 | −1.0000 | −2.1957E−03 | 5.7038E−03 | 1.4382E−02 |
| 9 | −1.0000 | 1.7300E−02 | −5.4558E−02 | −3.3348E−02 |
| 10 | −1.0000 | 2.0559E−02 | −2.8751E−02 | −1.9351E−02 |
| 11 | −1.0000 | 5.4084E−02 | −5.5518E−02 | −3.8369E−03 |
| 12 | −1.0000 | 3.9520E−02 | 4.5198E−02 | −2.7955E−02 |

TABLE 2-continued

| SURFACE | A6 | A7 | A8 | A9 |
|---|---|---|---|---|
| 4 | 2.2977E−05 | 1.0368E−07 | −6.3350E−07 | −6.9338E−08 |
| 5 | −2.3283E−03 | 8.3065E−05 | 1.7706E−04 | 5.3216E−05 |
| 6 | 5.9239E−03 | 3.5639E−03 | −4.8005E−04 | −5.6797E−04 |
| 7 | −4.2683E−02 | 2.4108E−02 | 1.1584E−02 | −9.3655E−03 |
| 9 | 1.1820E−01 | 1.5097E−02 | −1.9710E−01 | 1.6490E−01 |
| 10 | 4.2818E−03 | 6.7242E−03 | 1.3140E−03 | −1.6786E−03 |
| 11 | 8.6023E−03 | −1.1303E−03 | −7.2265E−04 | 2.6764E−04 |
| 12 | −5.1380E−03 | 2.1621E−03 | 5.9020E−04 | 4.8906E−06 |

| SURFACE | A10 | A11 | A12 | A13 |
|---|---|---|---|---|
| 4 | −5.7927E−09 | 3.1473E−11 | 1.9307E−10 | 3.2478E−11 |
| 5 | 1.4080E−05 | 6.0631E−07 | −1.4249E−06 | −8.0330E−07 |
| 6 | 5.1764E−06 | 2.1187E−05 | −1.2258E−05 | 1.2964E−05 |
| 7 | −7.6449E−03 | 8.0631E−03 | −2.0980E−03 | 6.2356E−05 |
| 9 | −3.8344E−02 | −4.5310E−03 | −7.4578E−04 | 5.6381E−04 |
| 10 | −1.4204E−04 | −1.2595E−04 | 1.5921E−05 | 6.7900E−05 |
| 11 | 1.1191E−04 | −1.3653E−05 | −5.7751E−05 | 6.4909E−06 |
| 12 | −6.5258E−06 | −9.7581E−06 | −5.6170E−06 | −2.6881E−06 |

| SURFACE | A14 | A15 | A16 | A17 |
|---|---|---|---|---|
| 4 | 5.4560E−12 | 8.1138E−13 | −1.3131E−13 | −3.0354E−14 |
| 5 | −8.7674E−08 | 2.5035E−08 | −1.3454E−09 | 3.3524E−09 |
| 6 | −1.1297E−06 | −6.9191E−07 | 1.0631E−07 | 3.1486E−10 |
| 7 | 7.7467E−06 | 5.8725E−06 | 5.6415E−08 | 3.7608E−10 |
| 9 | 2.5615E−04 | −5.1940E−15 | −4.4301E−13 | −1.1725E−14 |
| 10 | −8.2271E−06 | −6.8705E−07 | −4.8595E−08 | −7.2448E−14 |
| 11 | 6.9417E−06 | −1.1795E−06 | −3.1032E−08 | −1.2949E−10 |
| 12 | 1.7655E−06 | −2.4612E−08 | −4.9367E−08 | 6.4750E−09 |

| SURFACE | A18 | A19 | A20 |
|---|---|---|---|
| 4 | −3.5511E−15 | 3.0064E−16 | 5.8582E−17 |
| 5 | 2.5060E−11 | −1.2689E−18 | 5.3334E−20 |
| 6 | −3.5164E−16 | 4.6343E−17 | 4.8975E−20 |
| 7 | −7.0551E−16 | −8.1997E−18 | −2.1615E−19 |
| 9 | −2.7644E−16 | −7.3149E−18 | −1.9357E−19 |
| 10 | −1.1706E−16 | −8.2110E−18 | −2.1639E−19 |
| 11 | 4.9078E−12 | 1.2020E−17 | −2.1434E−18 |
| 12 | −6.8408E−11 | −7.6951E−20 | −2.9998E−19 |

Figure 6:
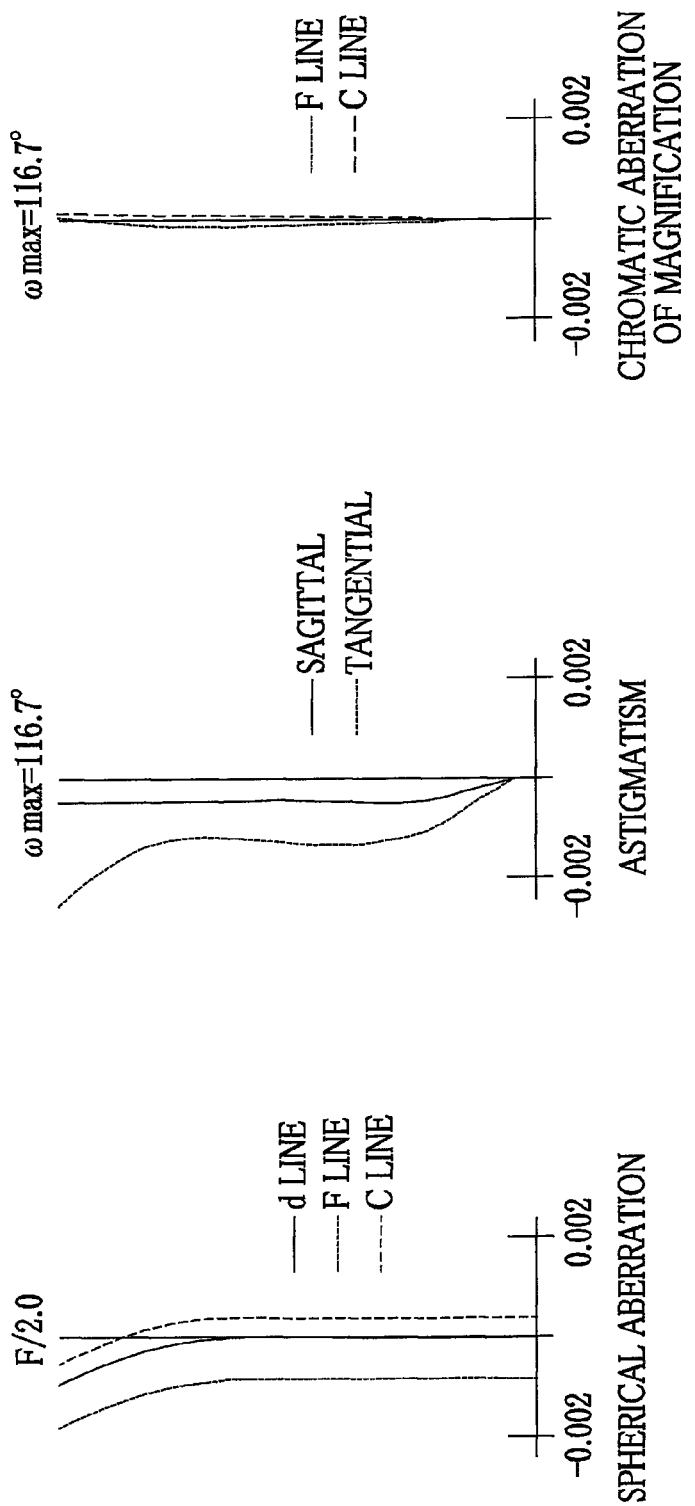
FIG. 6 is an aberration diagram of the imaging lens and transparent cover according to Embodiment 1.

FIG. 6 shows spherical aberration, astigmatism, and chromatic aberration of magnification under the configuration that the transparent cover 23 is disposed on the subject side of the imaging lens 20 and the cover glass 21 is disposed on the image side of the imaging lens 20. In the spherical aberration, d-line (wavelength of 587.6 nm) is shown with a solid line, F-line (wavelength of 486.13 nm) is shown with a first dashed line, and C-line (wavelength of 656.27 nm) is shown with a second dashed line which is a longer dashed line than the first dashed line. The astigmatism in sagittal direction is shown with a solid line and the astigmatism in tangential direction is shown with the first dashed line. In the chromatic aberration of magnification, F-line is shown with the first dashed line and C-line is shown with the second dashed line which is a longer dashed line than the first dashed line. Note that the lines showing the spherical aberration, astigmatism, and chromatic aberration of magnification, respectively are the same in Embodiment 2 which is described later.

In Embodiment 1, the focal length $f_D$ of the transparent cover 23 is −24.7 mm and the focal length $f_L$ of the imaging lens 20 is 1.5 mm. Accordingly, the value of $|f_D|/f_L$ is 16.5 which is within the range of the mathematical expression 1. Moreover, since the amount of $2\omega_{max}$ is 233°, which is within the range of the mathematical expression 3, and the amount of $2\omega_L$ is 159°, the value of $2\omega_{max}-2\omega_L$ is 74° which is within the range of the mathematical expression 2. Owing to this, the angle of view is widened more, and therefore even the lesion situated at the periphery of the transparent cover 23 can be captured. As shown in FIG. 6, the spherical aberration, astigmatism, and chromatic aberration of magnification are sufficiently corrected even if the angle of view is widened. Therefore, a clear image can be obtained even when the lesion situated at the periphery of the transparent cover 23 is captured.

Figure 7:
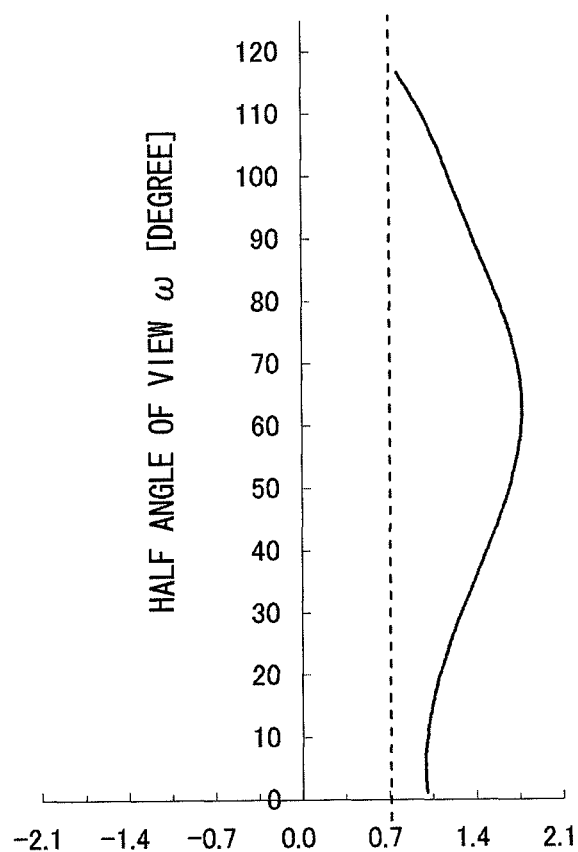
FIG. 7 is a graph illustrating distortion of the imaging lens and transparent cover according to Embodiment 1.

As shown in FIG. 7, the value of $(Y(\omega+\Delta\omega)-Y(\omega))/Y(\Delta\omega)$ is more than 0.7 over the entire range of the half angle of view $\omega$, and therefore the imaging lens 20 and transparent cover 23 are within the range of the mathematical expression 4. Owing to this, the distortion occurring at the periphery area of the image can be suppressed. As a result, the lesion appearing at the periphery of the image is not so distorted to the extent that it is overlooked, and therefore the lesion can be surely found.

[Embodiment 2]

Figure 8:
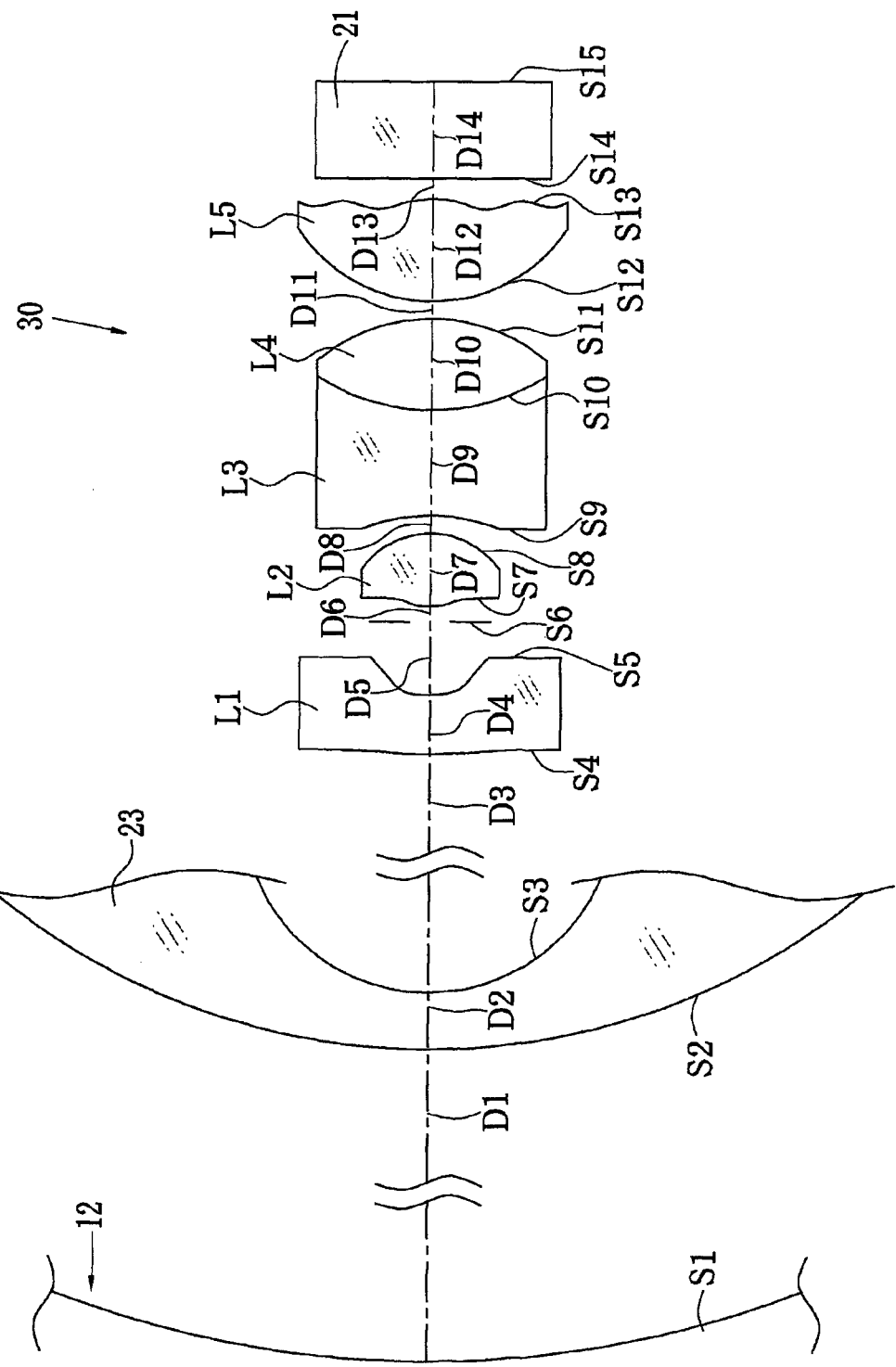
FIG. 8 is a cross-sectional view illustrating configurations of imaging lens and transparent cover according to Embodiment 2.

As shown in FIG. 8, an imaging lens 30 in Embodiment 2 includes five lenses of first lens L1 to fifth lens L5, and an aperture stop S6. Inside the capsule 13, the first lens L1, the aperture stop S6, the second lens L2, the third lens L3, the fourth lens L4, and the fifth lens L5 are arranged in this order from the side of the subject 12 of concave sphere. The third lens L3 and the fourth lens L4 constitutes a laminated lens. The transparent cover 23 is disposed between the subject 12 and the first lens L1.

Similarly to Embodiment 1, surfaces of the subject 12, the transparent cover 23, and the imaging lens 30 are represented by Si. That is, the surface of the subject 12 is S1, the surface of the transparent cover 23 on the subject side is S2, the surface of the transparent cover 23 on the image side is S3, the surface of the first lens L1 on the subject side is S4, the surface of the first lens L1 on the image side is S5, the aperture stop is S6, the surface of the second lens L2 on the subject side is S7, the surface of the second lens L2 on the image side is S8, the surface of the third lens L3 on the subject side is S9, the laminated surface of the third lens L3 is S10, the surface of the fourth lens L4 on the image side is S11, the surface of the fifth lens L5 of the subject side is S12, the surface of the fifth lens L5 of the image side is S13, the surface of the cover glass 21 on the subject side is S14, and surface of the cover glass 21 on the image side is S15. The surface S15 coincides with the imaging surface of the image sensor 14.

In addition, a distance between the surface Si and the surface S(i+1) (surface separation) in a direction of an optical axis of the imaging lens 30 is represented by Di. That is, a surface separation between the surfaces S1 and S2 is D1, a surface separation between the surfaces S2 and S3 is D2, a surface separation between the surfaces S3 and S4 is D3, a surface separation between the surfaces S4 and S5 is D4, a surface separation between the surfaces S5 and S6 is D5, a surface separation between the surfaces S6 and S7 is D6, a surface separation between the surfaces S7 and S8 is D7, a surface separation between the surfaces S8 and S9 is D8, a surface separation between the surfaces S9 and S10 is D9, a surface separation between the surfaces S10 and S11 is D10, a surface separation between the surfaces S11 and S12 is D11, a surface separation between the surfaces S12 and S13 is D12, a surface separation between the surfaces S13 and S14 is D13, and a surface separation between the surfaces S14 and S15 is D14.

The imaging lens 30 is designed based on lens data shown in Table 3 below.

TABLE 3

$f_L = 1.6$
$f_D = -19.3$
Fno = 2.0
$|f_D|/f_L = 12.1$
$2\omega_{max} = 243°$
$2\omega_L = 147°$
$2\omega_{max} - 2\omega_L = 96°$

| SURFACE | CURVATURE RADIUS | SURFACE SEPARATION | Nd | νd |
|---|---|---|---|---|
| OBJ | 45.8616 | 22.9308 | | |
| 2 | 31.7901 | 2.2931 | 1.58600 | 55.0 |
| 3 | 8.1454 | 8.3514 | | |
| 4* | 11.8912 | 2.4820 | 1.53039 | 55.2 |
| 5* | 1.2502 | 3.3004 | | |
| STOP | ∞ | 0.8239 | | |
| 7* | 7.8522 | 3.1590 | 1.53039 | 55.2 |
| 8* | -2.8809 | 0.7210 | | |
| 9 | -8.3637 | 4.5066 | 1.92286 | 18.9 |
| 10 | 8.9747 | 3.8677 | 1.72916 | 54.7 |
| 11 | -8.4625 | 0.9584 | | |
| 12* | 10.0245 | 4.3967 | 1.53039 | 55.2 |
| 13* | -2.5414 | 0.8537 | | |
| 14 | ∞ | 2.2931 | 1.55920 | 53.9 |
| 15 | ∞ | 0.0000 | | |
| IMG | ∞ | | | |

In Table 3, a symbol "*" in the column of the surface number indicates an aspheric surface. That is, the surfaces S4 and S5 of the first lens L1, the surfaces S7 and S8 of the second lens L2, and the surfaces S12 and S13 of the fifth lens L5 are the aspheric surfaces. The conic constant K and the aspherical constant Ai of the surfaces S4, S5, S7, S8, S12, and S13 are shown in Table 4.

TABLE 4

| SURFACE | K | A3 | A4 | A5 |
|---|---|---|---|---|
| 4 | -1.0000 | -4.1211E-03 | -2.0789E-03 | 1.6278E-04 |
| 5 | -1.0000 | -2.7379E-01 | 1.9759E-01 | -3.6734E-02 |
| 7 | -1.0000 | -4.2260E-03 | 1.1042E-03 | -3.9770E-03 |
| 8 | -1.0000 | -6.3453E-03 | 8.4601E-03 | -3.5200E-03 |
| 12 | -1.0000 | -5.6968E-03 | 7.0057E-03 | -1.0109E-03 |
| 13 | -1.0000 | 5.5962E-02 | 1.2624E-03 | -2.0759E-04 |

| SURFACE | A6 | A7 | A8 | A9 |
|---|---|---|---|---|
| 4 | 3.5252E-05 | 3.1255E-06 | -3.6575E-08 | -7.1605E-08 |
| 5 | -1.7317E-02 | 5.5113E-04 | 2.9509E-03 | 9.0608E-04 |
| 7 | -2.8140E-04 | 1.2269E-03 | 4.4777E-05 | -1.1980E-04 |
| 8 | 1.7387E-04 | 1.5704E-05 | 2.9431E-05 | -9.5373E-06 |
| 12 | -2.9044E-05 | 1.4767E-05 | 1.4667E-06 | -5.4865E-08 |
| 13 | -8.2208E-05 | -1.6629E-05 | -2.3223E-06 | -7.7639E-08 |

| SURFACE | A10 | A11 | A12 | A13 |
|---|---|---|---|---|
| 4 | -1.6083E-08 | -2.3358E-09 | -8.2106E-11 | 3.8892E-11 |
| 5 | -2.2020E-04 | -2.5128E-04 | 4.3420E-05 | 8.4058E-06 |
| 7 | -7.9379E-05 | -5.4175E-06 | 4.4506E-05 | -1.1955E-05 |
| 8 | -2.7177E-06 | -1.7337E-07 | -8.1997E-08 | 2.3964E-07 |
| 12 | -2.8382E-08 | -5.5487E-09 | -8.4172E-10 | -7.1694E-11 |
| 13 | 8.9311E-08 | -3.6021E-10 | 4.8163E-10 | 2.5386E-11 |

| SURFACE | A14 | A15 | A16 | A17 |
|---|---|---|---|---|
| 4 | 1.1935E-11 | 1.8169E-12 | -1.0312E-13 | -1.1082E-13 |
| 5 | -1.3497E-06 | -6.2400E-09 | 1.0999E-21 | 2.3984E-23 |
| 7 | -7.1950E-08 | 1.0389E-08 | -9.3374E-12 | 1.6927E-13 |
| 8 | 4.9096E-08 | -1.5338E-08 | -1.1340E-09 | -5.0901E-12 |
| 12 | 2.3969E-12 | 2.6410E-12 | 6.9906E-13 | 1.1607E-13 |
| 13 | 3.9097E-12 | 1.8067E-12 | 5.7627E-13 | 1.4867E-13 |

TABLE 4-continued

| SURFACE | A18 | A19 | A20 |
|---|---|---|---|
| 4 | −7.8781E−15 | 3.5945E−15 | −2.6606E−17 |
| 5 | −1.6746E−21 | −4.8517E−21 | −1.0594E−22 |
| 7 | 6.1835E−22 | 8.7018E−24 | 4.2216E−26 |
| 8 | 8.9804E−15 | 1.1404E−26 | 2.9399E−25 |
| 12 | −6.8918E−15 | −2.6120E−15 | 3.4009E−17 |
| 13 | 5.3552E−14 | −1.2354E−14 | −4.6038E−16 |

Figure 9:
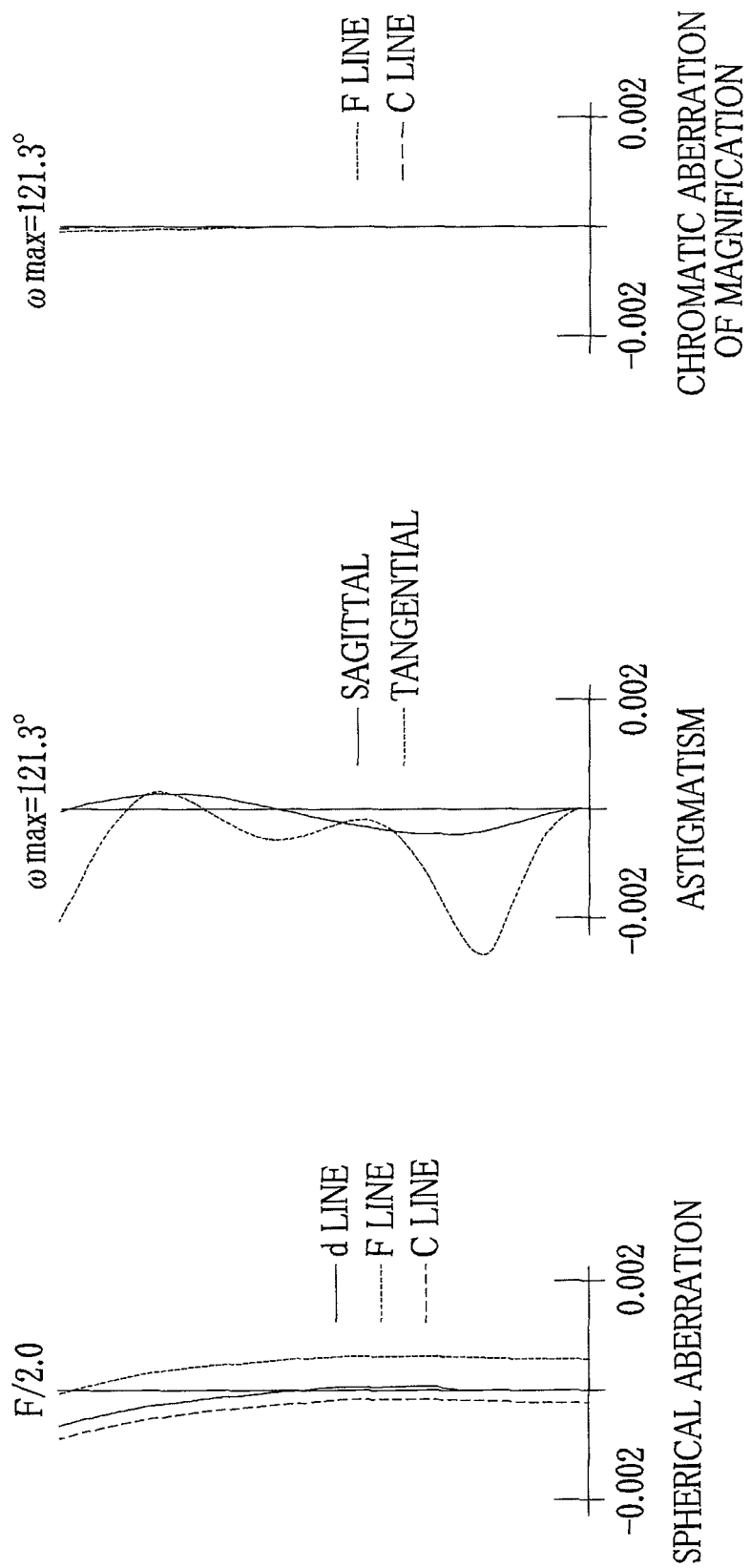
FIG. 9 is an aberration diagram of the imaging lens and transparent cover according to Embodiment 2.

FIG. 9 shows spherical aberration, astigmatism, and chromatic aberration of magnification under the configuration that the transparent cover 23 is disposed on the subject side of the imaging lens 30 and the cover glass 21 is disposed on the image side of the imaging lens 30.

In Embodiment 2, the focal length $f_D$ of the transparent cover 23 is −19.3 mm and the focal length $f_L$ of the imaging lens 30 is 1.6 mm. Accordingly, the value of $|f_D|/f_L$ is 12.1 which is within the range of the mathematical expression 1. Moreover, since the amount of $2\omega_{max}$ is 243°, which is within the range of the mathematical expression 3, and the amount of $2\omega_L$ is 147°, the value of $2\omega_{max}-2\omega_L$ is 96° which is within the range of the mathematical expression 2. Owing to this, the angle of view is widened more, and therefore even the lesion situated at the periphery of the transparent cover 23 can be captured. As shown in FIG. 9, the spherical aberration, astigmatism, and chromatic aberration of magnification are sufficiently corrected even if the angle of view is widened. Therefore, a clear image can be obtained even when the lesion situated at the periphery of the transparent cover 23 is captured.

Figure 10:
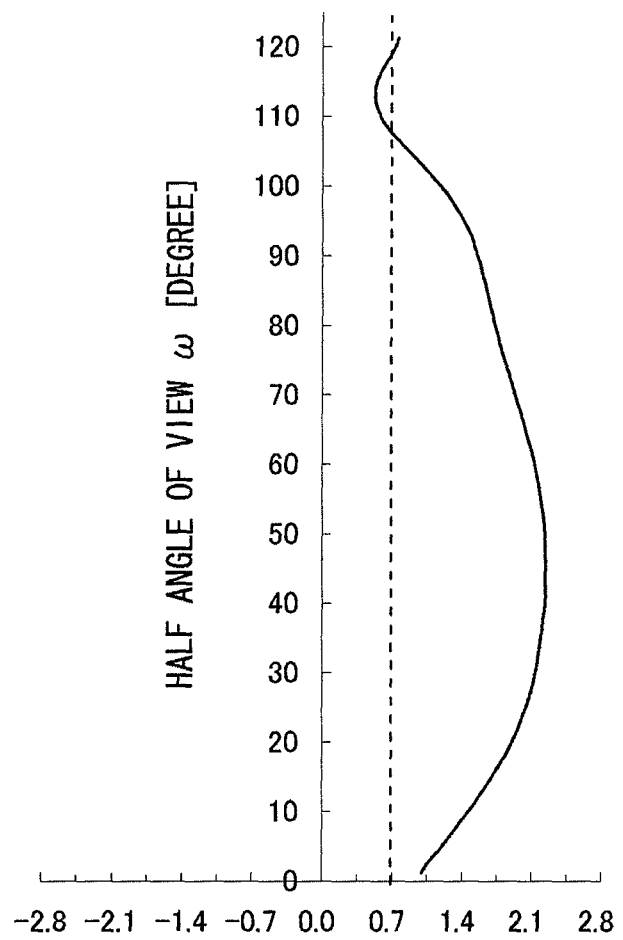
FIG. 10 is a graph illustrating distortion of the imaging lens and transparent cover according to Embodiment 2.

As shown in FIG. 10, the value of $(Y(\omega+\Delta\omega)-Y(())/Y(())$ is more than 0.7 over the almost entire range of the half angle of view (. Owing to this, the distortion can be suppressed.

DESCRIPTION OF THE REFERENCE NUMERALS

10: CAPSULE ENDOSCOPE
20: IMAGING LENS
23: TRANSPARENT COVER
L1: FIRST LENS
L2: SECOND LENS
L3: THIRD LENS
L4: FOURTH LENS

The invention claimed is:

1. A capsule endoscope comprising a hollow capsule body having an opening at its end, an imaging optical system provided inside said capsule body or provided to protrude from said opening of said capsule body, and a transparent cover attached to said end of said capsule body to cover said imaging optical system, wherein said transparent cover and said imaging optical system satisfy the following condition for imaging the inside of a body cavity of a patient:

$$|f_D|/f_L \leq 70$$

where $f_D$ is a focal length of said transparent cover, and $f_L$ is a focal length of said imaging optical system,
wherein said transparent cover includes a surface on the subject side and a surface on the image side, both of which is comprised of a spherical surface having a center axis on the optical axis.

2. The capsule endoscope according to claim 1 wherein said transparent cover and said imaging optical system further satisfy the following condition for imaging the inside of a body cavity of a patient:

$$2\omega_{max}-2\omega_L \geq 2.5$$

where $2\omega_{max}$ is a maximum angle of view of said imaging optical system and said transparent cover as a whole, and $2\omega_L$ is a maximum angle of view of said imaging optical system only.

3. The capsule endoscope according to claim 1, wherein the following condition is satisfied:

$$2\omega_{max} \geq 180°$$

where $2\omega_{max}$ is a maximum angle of view of said imaging optical system and said transparent cover as a whole.

4. The capsule endoscope according to claim 1, wherein the following condition is satisfied:

$$0.7<(Y(\omega+\Delta\omega)-Y(\omega))/Y(\Delta\omega)$$

where $Y(\omega)$ is an image height at an arbitrary angle of view $\omega$, and $\Delta\omega$ is an amount of slight change in said arbitrary angle of view $\omega$.

5. The capsule endoscope according to claim 1, wherein said imaging optical system comprises four lenses.

6. The capsule endoscope according to claim 1, wherein said imaging optical system comprises five lenses.

7. A capsule endoscope comprising a hollow capsule body having an opening at its end, an imaging optical system provided inside said capsule body or provided to protrude from said opening of said capsule body, and a transparent cover attached to said end of said capsule body to cover said imaging optical system, wherein said transparent cover and said imaging optical system satisfying the following condition for imaging the inside of a body cavity of a patient:

$$2\omega_{max}-2\omega_L \geq 2.5$$

where $2\omega_{max}$ is a maximum angle of view of said imaging optical system and said transparent cover as a whole, and $2\omega_L$ is a maximum angle of view of said imaging optical system only,
wherein said transparent cover includes a surface on the subject side and a surface on the image side, both of which is comprised of a spherical surface having a center axis on the optical axis.

8. The capsule endoscope according to claim 7, wherein the following condition is satisfied:

$$2\omega_{max} \geq 180°$$

where $2\omega_{max}$ is a maximum angle of view of said imaging optical system and said transparent cover as a whole.

9. The capsule endoscope according to claim 7, wherein the following condition is satisfied:

$$0.7<(Y(\omega+\Delta\omega)-Y(\omega))/Y(\Delta\omega)$$

where $Y(\omega)$ is an image height at an arbitrary angle of view $\omega$, and $\Delta\omega$ is an amount of slight change in said arbitrary angle of view $\omega$.

10. The capsule endoscope according to claim 7, wherein said imaging optical system comprises four lenses.

11. The capsule endoscope according to claim 7, wherein said imaging optical system comprises five lenses.

* * * * *